United States Patent [19]

Sachtler

[11] Patent Number: 5,326,925
[45] Date of Patent: Jul. 5, 1994

[54] ISOMERIZATION PROCESS FOR 2,3-DIMETHYLBUTANE PRODUCTION

[75] Inventor: J. W. Adriaan Sachtler, Des Plaines, Ill.

[73] Assignee: UOP, Des Plaines, Ill.

[21] Appl. No.: 812,384

[22] Filed: Dec. 23, 1991

[51] Int. Cl.$^5$ .............................. C07C 5/13
[52] U.S. Cl. .................. 585/736; 585/739; 585/741; 585/748
[58] Field of Search ............. 585/736, 739, 741, 748

[56] References Cited

U.S. PATENT DOCUMENTS

| 2,351,354 | 6/1944 | McMillan | 585/736 |
|---|---|---|---|
| 2,583,740 | 1/1952 | Kemp | 585/736 |
| 2,972,650 | 2/1961 | Burk et al. | 585/736 |
| 3,541,181 | 11/1970 | Bercik et al. | 585/736 |
| 4,144,282 | 3/1979 | McCaulay | 585/736 |
| 4,311,867 | 1/1982 | Takagawa et al. | 585/736 |
| 4,717,784 | 1/1988 | Stem et al. | 585/734 |
| 4,804,802 | 2/1989 | Evans et al. | 585/734 |

*Primary Examiner*—Patrick P. Garvin
*Assistant Examiner*—E. D. Irzinski
*Attorney, Agent, or Firm*—Thomas K. McBride; John G. Tolomei

[57] ABSTRACT

An isomerization process maximizes the production of 2,3-dimethylbutane by using an arrangement of two reaction zones that operate at low conversion conditions to maximize the production of a methyl pentane containing intermediate and limit the interconversion of 2,3-dimethylbutane to 2,2-dimethylbutane. The process converts a feed comprising normal hexane in a first reaction zone. The effluent from the first reaction zone has a high concentration of methyl pentanes which is separated from normal hexane and passed to a second separation section that receives the effluent from a second reaction zone. Methyl pentanes from the first and second reaction zone effluents enter the second reaction zone for conversion to dimethylbutane in a high 2,3-dimethylbutane to 2,2-dimethylbutane ratio. In this manner the process produces a principally dimethylbutane product having a relatively high octane rating as a result of the high 2,3-dimethylbutane concentration.

17 Claims, 2 Drawing Sheets

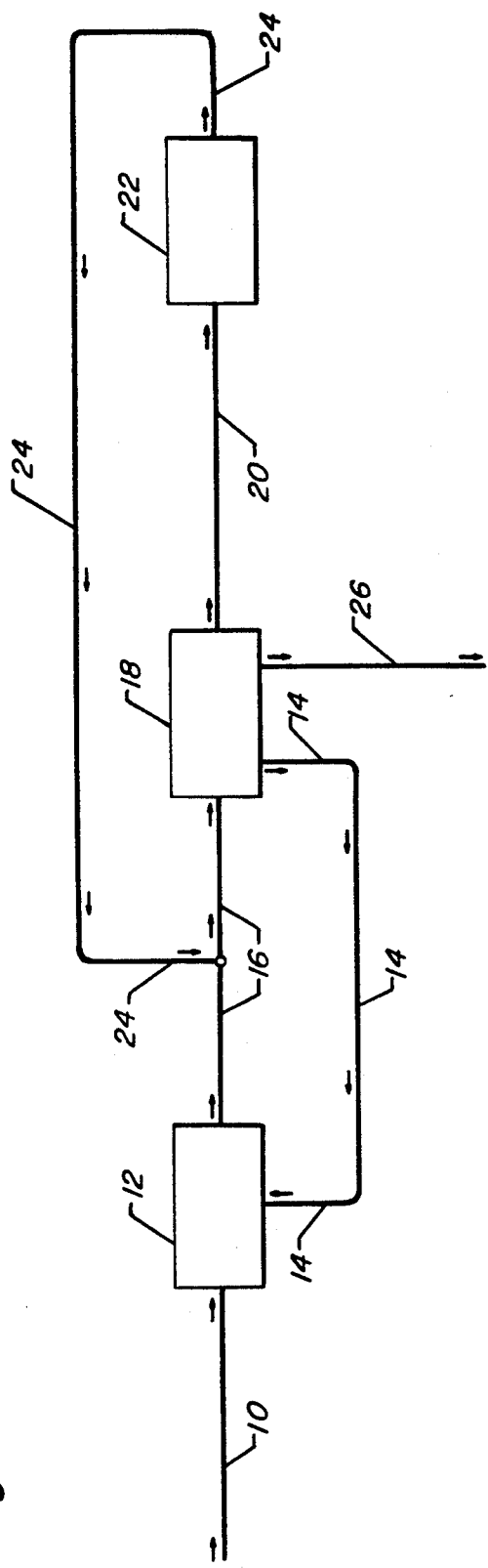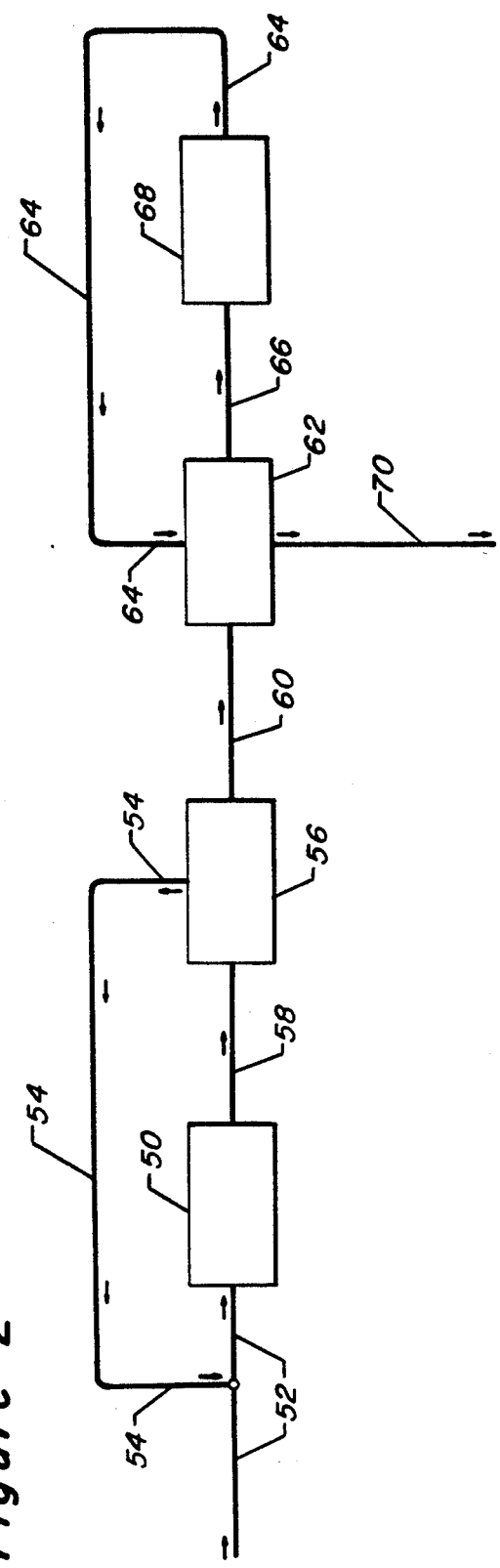
*Figure 1*
*Figure 2*

ISOMERIZATION PROCESS FOR 2,3-DIMETHYLBUTANE PRODUCTION

BACKGROUND OF THE INVENTION

1. Field of the Invention

This invention relates generally to isomerization processes. More specifically this invention relates to the isomerization of light paraffins, in particular $C_6$ paraffins.

2. Description of the Prior Art

Processes for the isomerization of paraffins into more highly branched paraffins are well known. New regulations affecting the composition of gasoline motor fuels have focused attention on isomerization to provide high octane pentane and hexane motor fuel components. A great deal of effort has been focused on maximizing the octane of isomerate streams by recovering and recycling the low-octane normal-paraffin isomers. In the more recent art, the octane of $C_6$ isomerate streams has been additionally increased by also recovering and recycling the methyl-pentanes to obtain additional dimethylbutanes (DMB)'s. However, in all the prior art processes for hexane isomerization, 2,2-DMB is maximized despite the fact that 2,3-DMB has a higher octane. This is because these processes all operate close to thermodynamic equilibrium, where the concentration 2,3-DMB is much lower than that of 2,2-DMB.

U.S. Pat. Nos. 4,717,784 and 4,804,802 disclose processes for the isomerization of a hydrocarbon feed and the use of adsorptive separation to generate normal paraffin and monomethyl-branched paraffin recycle streams. The effluent from the isomerization zone enters a molecular sieve separation zone that contains a 5A-type sieve and a ferrierite-type sieve that adsorb normal paraffins and monomethyl-branched paraffins, respectively. U.S. Pat. No. 4,804,802 discloses stream or hydrogen as the desorbent for desorbing the normal paraffins and monomethyl-branched paraffins from the adsorption section and teaches that steam or hydrogen may be recycled with the normal paraffins or monomethyl-branched paraffins to the isomerization zone.

BRIEF DESCRIPTION OF THE INVENTION

It is an object of this invention to maximize octane in an isomerization process by increasing the conversion of methyl pentanes to 2,3-DMB while preventing subsequent reaction to 2,2-DMB.

It has been discovered that the ratio of 2,3-DMB to 2,2-DMB may be readily increased in an isomerization process. 2,3-DMB has research octane of 105 versus an octane of 94 for 2,2-DMB butane. Accordingly, increasing the ratio of the 2,3 to 2,2 isomer will greatly improve the octane of the dimethylbutane isomerate components. Low conversion conditions are used to increase the octane of the $C_6$ isomerate components. The process of this invention can be used to increase overall octane by maximizing the amount of 2,3-DMB in the product stream or to reduce catalyst costs by using the lower conversion conditions to reduce reaction zone catalyst inventory.

It is generally believed that the isomerization reaction of hexane occurs as a series reaction: n-$C_6$=(2 MP+3 MP)=2,3-DMB=2,2-DMB. The interconversion between 2 MP and 3 MP is so fast as to be in equilibrium at commercially practical conditions. The reaction between the methyl pentanes and 2,3-DMB is faster than the subsequent reaction to 2,2-DMB. However, in the conventional high conversion processes, methyl pentanes are converted as much as possible to 2,2-DMB. The benefits of this invention are obtained by operating the isomerization zone in a non-traditional manner at lower conversion conditions that cause the methyl pentanes to react to 2,3-DMB, but prevent the subsequent conversion of 2,3-DMB to 2,2-DMB. In prior art processes, low conversion conditions for 2,3-DMB would also lower conversion of the normal paraffins, resulting in a prohibitively large amount of normal paraffin recycle. Therefore, the process of this invention separates normal paraffins from methyl pentanes and uses different reactors to separately convert the normal paraffin and methyl pentane streams. In this manner the normal paraffins are converted at conditions that will maximize methyl pentanes and the methyl pentanes are in turn converted at low conversion conditions that will increase the formation 2,3-DMB.

Accordingly in one embodiment, this invention is a process for the isomerization of a feedstream comprising $C_6$ hydrocarbons. The feedstream comprising the $C_6$ hydrocarbons is contacted with an isomerization catalyst at isomerization conditions in a first reaction zone to convert normal hexane to methyl pentanes and recover a first reaction zone effluent. At least a portion of the first reaction zone effluent is separated into a recycle stream comprising normal hexane and an intermediate feedstream comprising methyl pentanes. The intermediate feedstream and a recycle stream comprising methyl pentanes is contacted with an isomerization catalyst at low conversion isomerization conditions in a second reaction zone to convert methyl pentanes to 2,3-dimethylbutane and a second reaction zone effluent is recovered from the second reaction zone. At least a portion of the second reaction zone effluent is separated into a product stream comprising dimethylbutanes and the recycle stream comprising methyl pentanes.

In another embodiment, this invention is a process for the isomerization of a feedstream comprising $C_6$ hydrocarbons, wherein the process comprises contacting the feedstream comprising the $C_6$ hydrocarbons with an isomerization catalyst at isomerization conditions including a temperature of from 40°–300° C., a pressure of from 4 to 70 barsg, and a liquid hourly space velocity (LHSV) of from 1 to 40 in a first isomerization reaction zone to convert normal hexane to methyl pentanes and recovering a first reaction zone effluent; passing the first reaction zone effluent to a first separation section and recovering a recycle stream comprising normal hexane and an intermediate separation stream comprising the remainder of the first reaction zone effluent; passing the intermediate separation stream and a second reaction zone effluent stream to a second separation section and recovering an intermediate feedstream comprising methyl pentanes and a product stream comprising dimethylbutanes in a ratio of 2,3-DMB to 2,2-DMB of at least 0.3 from the second separation section; and contacting the intermediate feedstream with an isomerization catalyst at isomerization conditions including a temperature of from 0°–300° C., a pressure of from 4 to 70 barsg, and an LHSV of from 1 to 100 in a second reaction zone to convert methyl pentanes to dimethylbutane and produce the second reaction zone effluent.

BRIEF DESCRIPTION OF THE DRAWINGS

FIG. 1 is a schematic flow diagram of one embodiment of an isomerization process arranged in accordance with this invention.

FIG. 2 is a schematic flow diagram of an alternate embodiment of this invention.

DETAILED DESCRIPTION OF THE INVENTION

Figure 3:
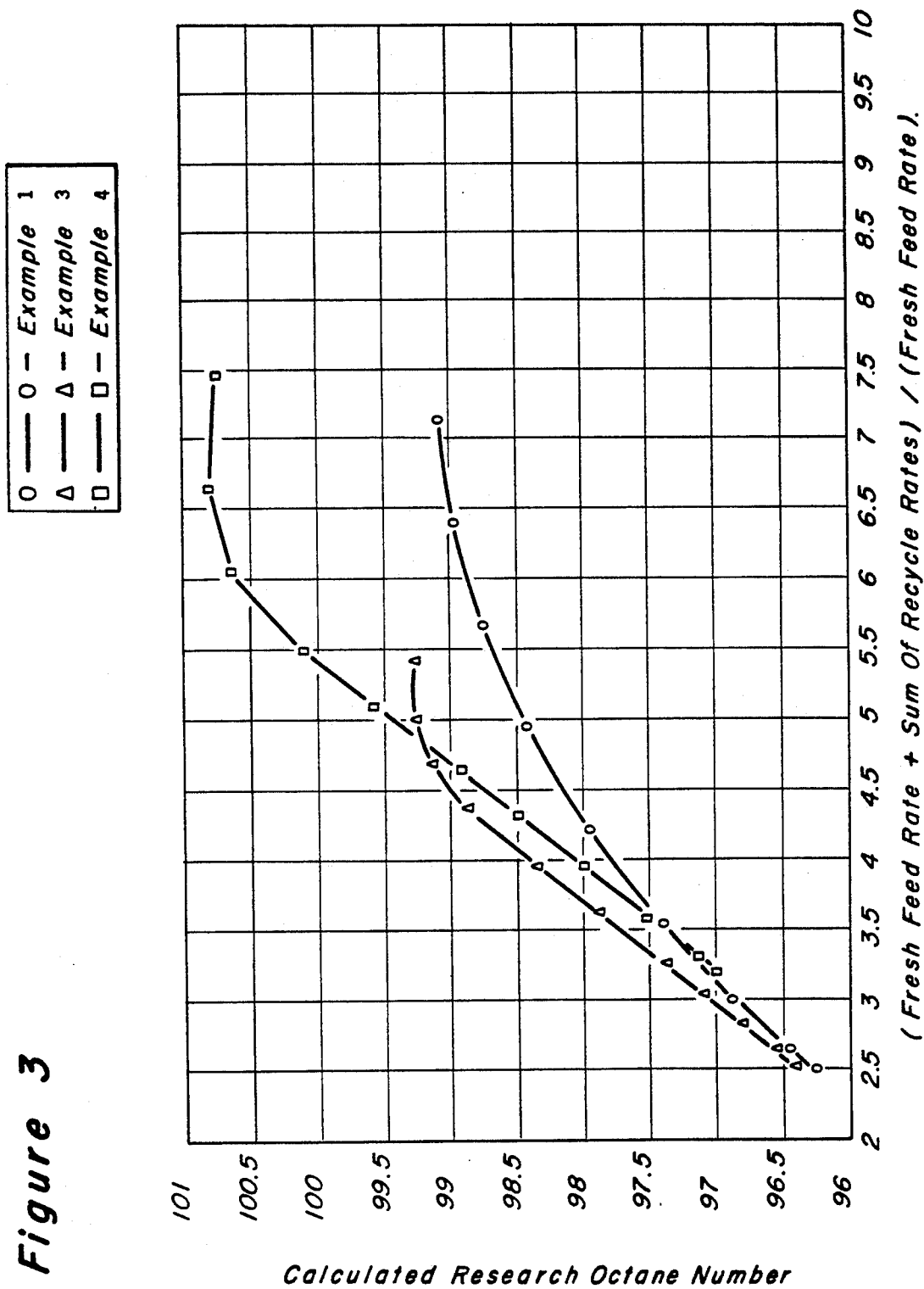
FIG. 3 is a graph comparing product octane with the total combined feed ratio for various process arrangements.

This invention uses a combination of two isomerization zones and a separation zone to convert $C_6$ paraffins to high octane products. The basic process arrangement is shown in FIG. 1. As depicted in FIG. 1, the process in its most basic form passes a hexane containing feed through line 10 to a reaction zone 12. A recycle line 14 returns normal paraffins to reaction zone 12. Reaction zone 12 operates at conditions for maximum conversion of normal paraffins to methyl pentanes; however, conversion of methyl pentanes to 2,2-DMB is limited in order to maximize the production of 2,3-DMB in the second reactor. A Line 16 passes the effluent from the isomerization zone to a separation zone 18. Separation zone 18 provides a methyl pentane stream that a line 20 carries to a reaction zone 22. Reaction zone 22 operates at low conversion conditions to maximize the conversion of methyl pentanes to 2,3-DMB and limit the production of 2,2-DMB. A line 24 recycles the effluent from reaction zone 22 to separation zone 18 via line 16. Normal paraffins entering separation zone 18 return to the reaction zone 12 via line 14 as previously described. A line 26 withdraws a product stream comprising 2,3 and 2,2-DMB.

Suitable feeds for the operation of this process will contain normal hexane. While this invention is particularly suited for the processing of $C_6$ paraffins, $C_5$ paraffins are also readily converted in the process. Thus, more typically feed mixtures for use in this process will include $C_5$ and $C_6$ hydrocarbon streams containing a substantial amount of normal hexane and monomethyl pentanes. Feedstocks that can be used in this invention include hydrocarbon fractions rich in $C_4$–$C_6$ normal paraffins and monomethyl pentanes. The term "rich" is defined as a stream having more than 50% of the above mentioned components. Preferred feedstocks are substantially pure normal paraffin and monomethyl pentane streams having from 5–6 carbon atoms. Other useful feedstocks include light natural gasoline, light straight run naphtha, gas oil condensates, light raffinates, light reformate, light hydrocarbons, and straight-run distillates having distillation end points of about 77° C. (170° F.) and containing substantial quantities of $C_4$–$C_6$ paraffins. The feed may also contain low concentrations of unsaturated hydrocarbons and hydrocarbons having more than 6 carbon atoms. The concentration of these materials should be limited to 10 wt. % for unsaturated compounds and 20 wt. % for heavier hydrocarbons in order to restrict hydrogen consumption in cracking reactions. $C_6$ paraffins provide the essential feed components for this invention. Therefore, feeds containing hydrocarbons other than $C_6$ hydrocarbons may undergo separation to concentrate $C_6$ hydrocarbons prior to passing the feed to the first isomerization zone of this invention.

This invention is based on the reaction kinetics for the isomerization of n-hexane. The general reaction scheme for normal hexane is summarized by the following equation:

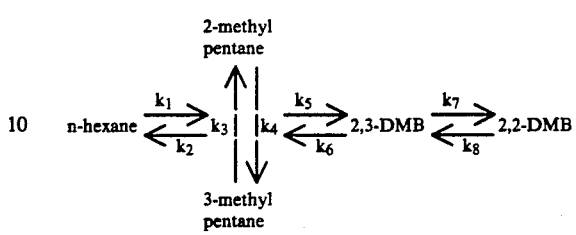

At most reaction conditions the kinetics of the various reactions result in a rapid interconversion between methyl pentanes and 2,3-DMB. For example, a HF-$BF_3$ acid catalyzed isomerization system at 25° C. will have forward rate constants of $k_1=12$, $k_3=116,000$, $k_5=58$ and $k_7=8.6$ and reverse rate constants of $k_2=1.5$, $k_4=58000$, $k_6=200$ and $k_8=1.5$. This invention is arranged so that methyl pentanes are converted to 2,3-DMB with little formation of normal hexane or 2,2-DMB. Therefore, to promote the conversion of methyl pentanes to 2,3-DMB, the process must be arranged to limit the production of 2,2-DMB. This is accomplished by adjusting the process conditions to lower the per pass conversion of the methyl pentanes. In order to ultimately achieve complete conversion of the methyl pentanes to 2,3-DMB, unreacted methyl pentanes are separated from the reactor effluent and recycled back to the reaction zone. Typically the process of this invention will produce a ratio of 2,3 dimethylbutane to 2,2 dimethylbutane of at least 0.3 and more preferably in a ratio of at least 0.5. In a particularly preferred form of this invention, the bulk of the methyl pentane conversion occurs in a separate reaction zone to enhance the effects of low conversion conditions. By performing the low conversion isomerization of methyl pentanes to 2,3-DMB in a separate reactor, high conversion of the normal paraffins in the first reactor can be maintained thereby preventing excessive recycle of unconverted normal paraffins. Therefore, the process of this invention will ordinarily use a first and a second reaction zone.

In most cases the feedstream entering the first reaction zone will include the fresh feed, a recycle stream of unconverted or partially converted hydrocarbons and hydrogen. Hydrogen is admixed with the feed in an amount that will provide a hydrogen to hydrocarbon molar ratio of from 0.01 to 10 in the effluent from the isomerization zone. Preferably, the hydrogen to hydrocarbon ratio is in the range of 0.05 to 5. Although no net hydrogen is consumed in the isomerization reaction, the isomerization zone will have a net consumption of hydrogen often referred to as the stoichiometric hydrogen requirement which is associated with a number of side reactions that occur. These side reactions include saturation of olefins and aromatics and cracking. For feeds having a high level of unsaturates, satisfying the stoichiometric hydrogen needs will require a higher hydrogen to hydrocarbon ratio for the feed at the inlet of the isomerization zone. Hydrogen in excess of the stoichiometric amounts for the side reactions is often maintained in the reaction zone to provide stability and increase conversion by compensating for variation in feedstream compositions that alter the stoichiometric hydrogen requirements. Higher hydrogen to hydrocarbon ratios are often used to prolong catalyst life by suppressing side reactions such as cracking and disproportionation. When such side reactions occur, they can reduce conversion and lead to formation of carbonaceous compounds, usually referred to as coke, that foul the catalyst. In some cases it has been found that the isomerization zone can operate with hydrogen to hydrocarbon ratios that provide effluent hydrogen concentrations below dissolved hydrogen levels. This means that for such processes the hydrogen in the effluent will be in a molar ratio of 0.01 to 0.05. When the hydrogen to hydrocarbon ratio in the effluent exceeds 0.05 it is usually not economically desirable to operate the isomerization zone without separate hydrogen recovery. Nevertheless, the process may operate with high or low hydrogen levels and those skilled in the art can provide the separators or other equipment for any necessary hydrogen recovery.

The feedstream and typically a recycle stream enter the first isomerization zone. Preferably, the first isomerization zone operates at moderately high conversion conditions designed to maximize the conversion of normal hexane to methyl pentanes while minimizing the formation of 2,2-DMB. A high conversion of normal hexane to methyl pentanes is obtained by recycling unconverted normal hexane to the first reaction zone. Any reaction zone configuration and catalyst system can be used for the first reaction zone as long as it provides high conversion. The catalyst compositions that can be used in the first reaction zone include platinum alumina catalyst with a Friedel-Crafts halide, platinum molecular sieve catalyst compositions, or platinum sulfate metal oxide catalyst systems.

The preferred catalyst for the isomerization reaction zones is a chlorided platinum alumina catalyst. The alumina is preferably an anhydrous gamma-alumina with a high degree of purity. The catalyst may also contain other platinum group metals. The term platinum group metals refers to noble metals excluding silver and gold which are selected from the group consisting of platinum, palladium, ruthenium, rhodium, osmium, and iridium. These metals demonstrate differences in activity and selectivity such that platinum has now been found to be the most suitable for this process. The catalyst will contain from about 0.05 to 2 wt. % of the platinum. Other platinum group metals may be present in a concentration of from 0.01 to 2 wt. %. The platinum component may exist within the final catalytic composite as an oxide or halide or as an elemental metal. The presence of the platinum component in its reduced state has been found most suitable for this process. The chloride component is present in an amount from about 2 to about 10 wt. % based upon the dry support material. The use of chloride in amounts greater than 4 wt. % have been found to be the most beneficial for this process. The inorganic oxide preferably comprises alumina and more preferably gamma-alumina, eta-alumina, and mixtures thereof.

There are a variety of ways for preparing the catalytic composite and incorporating the platinum metal and the chloride therein. In one such method the catalyst is prepared by impregnating the carrier material through contact with an aqueous solution of a water-soluble decomposable compound of the platinum group metal. For best results, the impregnation is carried out by dipping the carrier material in a solution of chloroplatinic acid. Alternative solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of halogen must be incorporated into the catalyst by the addition or formation of aluminum chloride to or on the platinum-aluminum catalyst base.

It is generally known that highly chlorided platinum-alumina catalysts of this type are highly sensitive to sulfur and oxygen-containing compounds. Therefore, the use of such catalysts requires that the feedstock be relatively free of such compounds. A sulfur concentration no greater than 0.5 ppm is generally required. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water can act to permanently deactivate the catalyst by removing high activity chloride from the catalyst and replacing it with inactive hydroxide. Therefore, water, as well as oxygenates, in particular $C_1$–$C_5$ oxygenates, that can decompose to form water, can only be tolerated in very low concentrations. In general, this requires a limitation of oxygenates in the feed to about 0.1 ppm or less. The feedstock may be treated by any method that will remove water and sulfur compounds. Sulfur may be removed from the feedstream by hydrotreating. A variety of commercial dryers are available to remove water from the feed components. Adsorption processes for the removal of sulfur and water from hydrocarbon streams are also well known to those skilled in the art.

Another catalyst composition for use in the present invention comprises a Group VIII noble metal, a hydrogen form crystalline alumino-silicate, and a refractory inorganic oxide with said catalyst composition having a high surface area. Preferably the surface area will be above 580 $m^2/g$. Significant improvements in isomerization performance are realized when the surface area of the catalytic composition is at or above 580 $m^2/g$. The Group VIII noble metal is again incorporated into the catalytic composite to supply the hydrogenation-dehydrogenation function and the preferred Group VIII noble metal is platinum. The Group VIII noble metal is present in an amount from about 0.1 to about 5% by weight of the composite and preferably in an amount of at least about 0.15% by weight, but not over 0.5% by weight. The catalytic composite may also contain a catalytically effective amount of a promoter metal such as tin, lead, germanium, cobalt, nickel, iron, tungsten, chromium, molybdenum, bismuth, indium, gallium, cadmium, zinc, uranium, copper, silver, gold, tantalum, or one or more of the rare earth metals and mixtures thereof. The hydrogen form silica-alumina has either a three-dimensional or channel-pore-structure crystal lattice framework. The three-dimensional alumino-silicates include both synthetic and naturally occurring silica aluminas, such as, the faujasites which include X-type, Y-type, ultrastable-Y and the like. L-type, omega-type, and mordenite are examples of the channel-pore-structure crystalline alumino-silicates. Mordenite in either naturally occurring or synthetic form are preferred, particularly with a silica to alumina ratio of at least 16:1. The hydrogen form alumino-silicate may be present in an amount within the range of 50 to about 99.5 wt. %, preferably within the range of 75 to about 95 wt. %, and the refractory inorganic oxide may be present in an amount within the range of from 0.5 to about 50 wt. %. The inorganic oxide preferably comprises alumina and more preferably gamma-alumina, eta-alumina and mixtures thereof.

Operating conditions within the first isomerization zone are selected to maximize the production of methyl pentanes from the normal hexane feed component. Temperatures within the first reaction zone can range from about 40°–300° C. Lower reaction temperatures are generally preferred since they usually favor equilibrium mixtures of isoalkanes versus normal alkanes. When the feed mixture is primarily $C_6$ alkanes and the catalyst is a highly chlorided platinum alumina, temperatures in the range of from 60° to 160° C. are preferred. The reaction zone may be maintained over a wide range of pressures. Pressure conditions in the isomerization of $C_5$–$C_6$ paraffins range from 4 barsg to 70 barsg. Preferred pressures for this process are in the range of from 15 barsg to 40 barsg.

In accordance with this invention, the feed rate to the first reaction zone can vary over a wide range. The first reaction zone operates a conversion conditions that are reduced relative to the high conversion conditions usually practiced in the art. While operation of the first reaction zone at high conversion conditions which maximize conversion of the normal hexane component to DMB's as well as methyl pentanes has the advantage of minimizing overall process recycle, such high conversion conditions result in a relatively high conversion of methyl pentanes to 2,2-DMB. Thus, reduced or moderate conversion conditions for the first reaction zone are usually favored to maximize production of methyl pentanes, which in turn maximizes the total production of 2,3-DMB by the overall process. Therefore, the ratio of feed volume rate to catalyst volume, referred to herein as liquid hourly space velocity (LHSV) ranges from 1 to 40 hr.$^{-1}$, however, LHSV's of between 5 to 30 hr.$^{-1}$ are preferred in the first isomerization zone to maximize the production of methyl pentanes and overall octane. As an alternative to increasing the LHSV to very high values, which at some point would cause mass transfer limitations and pressure drop problems, the reactor temperature may be lowered to achieve the desired low per-pass conversion.

Operating conditions within the second isomerization zone are selected to maximize the production of 2,3-DMB. Temperatures within the second reaction zone can range from about 0° to 300° C. From an equilibrium standpoint, higher temperatures favor the production of 2,3-DMB over 2,2-DMB; however, this invention is based on keeping conversion low in the second reaction zone and avoiding equilibrium conditions. One approach to a low conversion second reaction zone is a combination of high temperature and high space velocity. Since ultra high space velocities usually pose operational problems, a combination of low reaction temperatures and moderate space velocity generally provides the most practical approach to obtaining a high production of 2,3-DMB in the second reaction zone. The lower temperature will control the kinetics of the second reaction zone to limit the reaction of 2,3-DMB to 2,2-DMB. When the feed mixture is primarily $C_6$ alkanes and the catalyst is a highly chlorided platinum alumina, temperatures in the range of from 40° to 140° C. are preferred. The reaction zone may be maintained over a wide range of pressures. Pressure conditions in the isomerization of $C_5$–$C_6$ paraffins range from 4 barsg to 70 barsg. Preferred pressures for this process are in the range of from 15 barsg to 40 barsg. The feed rate to the second reaction zone is kept relatively high to maintain low conversion conditions. These conditions include LHSV's ranging from 1 to 100 hr.$^{-1}$, however, space velocities between 10 to 60 hr.$^{-1}$ are preferred in the second isomerization zone to maximize the production of 2,3-DMB by shifting the conversion away from the production of 2,2-DMB. Thus the second isomerization zone will usually operate at a moderately high LHSV and low temperature.

The combination of high LHSV in the first and second reaction zone has the advantage of greatly reducing the overall catalyst requirements of the process. In many instances, the catalyst requirements for the two reaction zones of this invention may be lower than the catalyst requirements of a single reaction zone from the prior art.

Operation of either reaction zone with the preferred chlorided platinum-alumina catalyst also requires the presence of a small amount of an organic chloride promoter. The organic chloride promoter serves to maintain a high level of active chloride on the catalyst as low levels are continuously stripped off the catalyst by the hydrocarbon feed. The concentration of promoter in the reaction zone is maintained ar from 30 to 300 mass ppm based on hydrocarbon feed. The preferred promoter compound is carbon tetrachloride. Other suitable promoter compounds include oxygen-free decomposable organic chlorides such as isopropylchloride, butylchloride, ethylene tetrachloride, and chloroform to name only a few of such compounds. The need to keep the reactants dry is reinforced by the presence of the organic chloride compound which may convert, in part, to hydrogen chloride. As long as the process streams are kept dry, there will be no adverse effect from the presence of small amounts of hydrogen chloride.

The effluent from the first reaction zone is passed to a separation zone. Ideally the separation zone will separate the effluent from the first and second reaction zones into: a normal paraffin recycle stream that contains all of the unreacted normal paraffins; a product stream having all $C_5$ and lower isoparaffins, and DMB's; and a feedstream for the second isomerization zone that contains any methyl pentanes. This invention is not limited to a particular method of separation. The invention can use any type of separation zone that will approach the ideal separation. The separation zone can include any number of separation sections which can use adsorption, fractionation, membranes or other separation technologies. Preferably the separation zone will also remove cyclic hydrocarbons from the second isomerization zone feedstream. Since the second reaction zone operates at low conversion conditions little if any conversion of cyclic hydrocarbons will occur. Absent removal, cyclic hydrocarbons will build up in the feedstream to the second reaction zone and inhibit methyl pentane conversion in the second reaction zone.

The separation zone may consist of more than one separation section. FIG. 2 shows such an arrangement wherein a hexane containing feed enters a reaction zone 50 via a line 52 along with recycled normal paraffins carried by a line 54. An effluent containing normal paraffins and methyl pentanes passes from reactor 50 to a separation section 56 via a line 58. Separation section 58 recovers normal paraffins for recycle to the first reaction zone via line 54 and passes the remainder of the second reaction zone effluent to a second separation section 62 via a line 60. Second separation section 62 also receives a second reaction zone effluent via a line 64. A line 66 passes a methyl pentane containing stream from separation section 62 to a second reaction zone 68. Second reaction zone 68 operates at low conversion conditions to provide a 2,3-DMB containing stream that is returned to separation zone 62 via line 64. Separation section 62 recovers the DMB's in a product stream carried by line 70. In such an arrangement any $C_5$ hydrocarbons present in the process will be recovered with the DMB product stream.

When the separation zone is composed of multiple separation sections, the different separation sections may use different principles of separation. For example, in a typical arrangement of the process embodiment of FIG. 2 section 56 will comprise an adsorptive separation section and the separation section 62 may comprise a distillation column such as a deisohexanizer. Adsorptive separation section 56 uses a shape selective adsorbent to retain normal paraffins and exclude branched chain paraffins. A wide variety of adsorptive separations systems are well known to those skilled in the art for adsorptively separating normal paraffins from mixtures of normal paraffins and isoparaffins. One such system that operates in liquid phase is described in U.S. Pat. No. 2,985,589 issued to D. B. Broughton. In a typical $C_5$-$C_6$ isomerization section, the first reaction zone effluent that enters the adsorptive separation zone will contain normal paraffins, isopentane, methyl pentanes and some DMB's. The first reaction zone recovers the majority of the normal paraffins and rejects isopentane methyl pentanes and DMB's which are passed on to separation section 62. In addition to the isopentane, methyl pentanes and DMB's from the first separation section, and additional DMB's and unconverted methyl pentanes from the second reaction zone enter separation section 62. Separation section 62 can use distillation to separate the higher boiling isopentane and DMB's from the methyl pentanes that are returned to reaction zone 68. While a deisohexanizer can be used for separation section 62, ordinary deisohexanizer arrangements will not provide the maximum benefit of this invention due to the small boiling point difference between 2 methyl pentane and 2,3-DMB. Therefore the advantages of this invention are maximized by providing a good separation between the 2 methyl pentane and the 2,3-DMB. Alternate separation methods for separation section 62 include adsorptive separation techniques.

ILLUSTRATIVE EMBODIMENTS

The benefits of this invention are demonstrated by the following examples which are based on computer simulations of isomerization reaction zones. The conversions and separations calculated in these examples are based in part on data obtained from commercially operating units and pilot plant studies. All of the examples use a normal hexane feed that is processed in one or more isomerization zones. Each of the isomerization zones operates at a constant temperature and contains a high purity gamma alumina catalyst that contains between 0.1 to 0.5 wt. % of a platinum metal and from about 4 to 10 wt. % of a chloride component.

EXAMPLE 1

This example demonstrates the advantages that the operational aspects of this invention have on a conventional isomerization flow scheme. In this example the normal hexane feed is passed through a single isomerization zone to produce a DMB product stream. All but about 1% of the unconverted normal hexane and methyl pentane products were recycled with the feed to the inlet of the reaction zone. As a result, the product stream was essentially a mixture of DMB isomers. The example demonstrates the effect of reducing conversion on the product by varying the feed rate to a fixed quantity of catalyst. Table 1 lists the results of the differing feed rates. Table 1 also lists values for total CFR which is defined as the sum of the feed rate and any recycle rates divided by the feed rate. A review of the data in FIG. 3 demonstrates that a lower per pass conversion of the combined feed, which corresponds to an increase in the combined feed ratio, raises the octane of the DMB product. As indicated by Table 1, this increase in octane is caused by the increased production of higher octane 2,3-DMB, both in absolute concentration and relative to 2,2-DMB.

TABLE 1

| LHSV | TOTAL CFR | RON | wt. % 2,2-DMB | wt. % 2,3-DMB |
|---|---|---|---|---|
| 2.5 | 2.48 | 96.3 | 73.8 | 24.7 |
| 5.3 | 2.63 | 96.5 | 71.6 | 26.8 |
| 9.0 | 2.99 | 96.9 | 66.3 | 31.7 |
| 14.2 | 3.55 | 97.4 | 59.0 | 38.4 |
| 21.1 | 4.22 | 98.0 | 51.1 | 45.6 |
| 29.7 | 4.94 | 98.4 | 43.5 | 52.5 |
| 39.8 | 5.68 | 98.8 | 36.8 | 58.5 |
| 51.4 | 6.41 | 99.0 | 31.0 | 63.5 |
| 64.4 | 7.15 | 99.1 | 26.1 | 67.7 |

EXAMPLE 2

This example demonstrates the effects of recycling essentially only the normal hexane component from the reaction zone of Example 1. The single reaction zone of this example operates in essentially the same manner as the reaction zone of Example 1 except that about 99% of the normal hexane and about 1% of the other effluent hydrocarbons were recycled with the feed to the first reaction zone. The results of Example 2 are listed in Table 2. Example 2 shows that as conversion decreases, the overall product octane decreases when there is no substantial recycle of methyl pentanes. Nevertheless, the decrease in conversion still generally increases the relative production of 2,3-DMB to 2,2-DMB. Therefore while the lower conversion conditions as used in this example will increase the ratio of 2,3-DMB to 2,2-DMB it does not increase the overall level of DMB's and is therefore not an advantageous arrangement.

TABLE 2

| LHSV | CFR | RON | wt. % 2,2-DMB | wt. % 2,3-DMB | wt. % MP |
|---|---|---|---|---|---|
| 1.1 | 1.14 | 84.7 | 34.0 | 11.3 | 54.5 |
| 3.4 | 1.14 | 84.6 | 33.1 | 11.4 | 55.3 |
| 5.8 | 1.16 | 84.0 | 29.4 | 12.0 | 58.5 |
| 8.3 | 1.19 | 83.3 | 24.7 | 12.6 | 62.5 |
| 11.1 | 1.24 | 82.6 | 20.3 | 13.2 | 66.3 |
| 14.4 | 1.31 | 82.0 | 16.4 | 13.6 | 69.6 |
| 18.4 | 1.41 | 81.4 | 13.1 | 14.0 | 72.5 |
| 23.3 | 1.55 | 80.8 | 10.4 | 14.2 | 75.0 |
| 29.8 | 1.75 | 80.3 | 8.0 | 14.3 | 76.9 |
| 38.7 | 2.04 | 79.8 | 6.0 | 14.2 | 78.7 |

EXAMPLE 3

By this example the advantages of the dual reaction zone system of this invention are demonstrated. In this example, the effluent from the single reaction zone of Example 2 provides the feed for a second reaction zone. A combination of a relatively high conversion first reaction zone and a low conversion second reaction zone were investigated by using the product corresponding to a 3.4 LHSV in Table 2 as the feed to a second reaction zone. The LHSV of the feed to the second reaction zone was varied over a wide range to show the effect of decreased conversion. Effluent from the second reaction zone was separated and about 99% of any unconverted methyl pentanes along with about 1% of the DMB was recycled to the second reaction zone. The results of Example 3 are shown in Table 3 and demonstrate that the second reaction zone will increase the resultant product to the same octane levels as the product obtained by Example 1. However, the second reaction zone achieves the maximum octane at much higher space velocities and a reduced Total CFR relative to Example 1. Therefore, the two reaction zones of this invention have the advantage of lowering overall recycle rates while increasing the octane of the final product. FIG. 3 provides a comparison of the octane obtained by the examples as a function of total recycle ratio.

TABLE 3

| LHSV | TOTAL CFR | RON | wt. % 2,2-DMB | wt. % 2,3-DMB |
|---|---|---|---|---|
| 1.4 | 2.51 | 96.4 | 73.7 | 25.0 |
| 4.2 | 2.54 | 96.4 | 73.2 | 25.4 |
| 7.6 | 2.66 | 96.6 | 71.4 | 27.1 |
| 11.9 | 2.84 | 96.8 | 68.5 | 29.8 |
| 17.2 | 3.06 | 97.1 | 65.1 | 33.0 |
| 23.3 | 3.27 | 97.4 | 61.7 | 36.2 |
| 37.2 | 3.63 | 97.9 | 55.8 | 41.7 |
| 56.2 | 3.96 | 98.3 | 50.5 | 46.7 |
| 96.6 | 4.37 | 98.9 | 44.1 | 52.6 |
| 141.2 | 4.68 | 99.1 | 40.7 | 55.8 |
| 192.9 | 5.01 | 99.3 | 38.5 | 57.6 |
| 255.8 | 5.42 | 99.3 | 37.1 | 58.6 |

EXAMPLE 4

Example 4 demonstrates how another method of operating the process of this invention provides a further improvement in product octane. The operation of the process in Example 4 was essentially the same as Example 3 except that the first reaction zone operated at an LHSV of 18.4 and produced the corresponding effluent as listed in Table 2. Table 4 lists the results of Example 4 and together with Table 3 establishes that an increased octane product is obtained with a low conversion first reaction zone and second reaction zone that operates in accordance with this invention. In addition, the very high LHSV of the first and second reaction zones in Example 4 show that the overall catalyst requirements of the two reaction zone arrangement is lower than the overall catalyst requirements of the single reaction zone system depicted by Example 1.

TABLE 4

| LHSV | TOTAL CFR | RON | wt. % 2,2-DMB | wt. % 2,3-DMB |
|---|---|---|---|---|
| 1.8 | 3.20 | 97.0 | 66.5 | 31.7 |
| 5.7 | 3.30 | 97.1 | 65.0 | 33.1 |
| 10.9 | 3.59 | 97.5 | 60.6 | 37.2 |
| 17.8 | 3.96 | 98.0 | 54.8 | 42.7 |

TABLE 4-continued

| LHSV | TOTAL CFR | RON | wt. % 2,2-DMB | wt. % 2,3-DMB |
|---|---|---|---|---|
| 26.1 | 4.32 | 98.5 | 48.9 | 48.1 |
| 35.4 | 4.63 | 99.0 | 43.9 | 52.9 |
| 55.3 | 5.10 | 99.6 | 36.2 | 60.0 |
| 81.6 | 5.50 | 100.1 | 30.0 | 65.8 |
| 139.3 | 7.76 | 100.6 | 23.2 | 72.1 |
| 209.5 | 6.66 | 100.8 | 19.6 | 75.1 |
| 301.6 | 7.45 | 100.8 | 17.4 | 76.5 |

I claim:

1. A process for the isomerization of a feedstream comprising $C_6$ hydrocarbons, said process comprising:
    (a) contacting said feedstream comprising said $C_6$ hydrocarbons with an isomerization catalyst at isomerization conditions including a temperature of from 40°–300° C., a pressure of from 4 to 70 barsg and a Liquid Hourly Space Velocity of from 1 to 40 hrs$^{-1}$ in a first reaction zone to convert normal hexane to methyl pentanes and recovering a first reaction zone effluent;
    (b) separating at least a portion of said first reaction zone effluent into a first recycle stream comprising normal hexane and an intermediate feedstream comprising methyl pentanes;
    (c) contacting a combined feed comprising said intermediate feedstream and a second recycle stream comprising methyl pentanes with an isomerization catalyst at isomerization condition including a temperature of from 0°–300° C., a pressure of from 4 to 70 barsg, and a Liquid Hourly Space Velocity of from 1 to 100 hrs$^{-1}$ in a second reaction zone to convert methyl pentanes to 2,3-dimethylbutane and recovering a second reaction zone effluent;
    (d) separating at least a portion of said second reaction zone effluent into a product stream comprising dimethylbutanes and said second recycle stream comprising methyl pentanes; and
    (e) recovering said product stream from said process.

2. The process of claim 1 wherein said isomerization catalyst in at least one of said first reaction zone and said second reaction zone comprises a platinum group metal on a chlorided alumina base.

3. The process of claim 1 wherein said isomerization catalyst in at least one of said first reaction zone and said second reaction zone comprises a Group VIII noble metal, a hydrogen form aluminosilicate, and/or refractory inorganic oxide.

4. The process of claim 1 wherein the isomerization catalyst in said first and second reaction zones have the same composition.

5. The process of claim 1 wherein said first reaction zone effluent enters a first separation zone that separates said first reaction zone effluent into said first recycle stream comprising normal hexane and said intermediate feedstream, said intermediate feedstream and a said second reaction zone effluent enter a second separation zone and said second separation zone produces said product stream comprising dimethylbutanes and said combined feedstream.

6. The process of claim 1 wherein said first separation section is an adsorptive separation section and said second separation section is a rectification section.

7. The process of claim 1 wherein said feedstream is treated for the removal of cyclic hydrocarbons before said stream enters said first reaction zone.

8. The process of claim 1 wherein said product stream has a mole ratio of 2,3 dimethylbutane to 2,2 dimethylbutane of at least 3.

9. The process of claim 1 wherein said product stream has a mole ratio of 2,3-dimethylbutane to 2,2-dimethylbutane of at least 0.5.

10. A process for the isomerization of a feedstream comprising $C_6$ hydrocarbons, said process comprising:
   (a) contacting said feedstream comprising said $C_6$ hydrocarbons with an isomerization catalyst at isomerization conditions including a temperature of from 40°-300° C., a pressure of from 4 to 70 barsg, and a liquid Hourly Space Velocity of from 5 to 30 hrs$^{-1}$ in a first reaction zone to convert normal hexane to methyl pentanes and recovering a first reaction zone effluent;
   (b) passing said first reaction zone effluent to a first separation section and recovering a recycle stream comprising normal hexane and an intermediate separation stream comprising the remainder of said first reaction zone effluent from said second separation section;
   (c) passing said intermediate separation stream and a second reaction zone effluent stream to a second separation section and recovering an intermediate feedstream comprising methyl pentanes and a product stream comprising dimethylbutanes in a ratio of 2,3-DMB to 2,2-DMB of at least 0.3 from said second separation section;
   (d) contacting said intermediate feedstream with an isomerization catalyst at isomerization conditions including a temperature of from 0°-300° C., a pressure of from 4 to 70 barsg, and a Liquid Hourly Space Velocity of from 10 to 60 hrs$^{-1}$ in a second reaction zone to convert methyl pentanes to dimethylbutane and recovering said second reaction zone effluent;
   (e) recovering said product stream from said isomerization zone.

11. The process of claim 10 wherein said first separation section comprises an adsorptive separation section and said second separation section comprises a deisohexanizer column.

12. The process of claim 10 wherein said product stream has a mole ratio of 2,3-dimethylbutane to 2,2-dimethylbutane of at least 0.5.

13. The process of claim 10 wherein said feedstream comprises $C_5$ and $C_6$ hydrocarbons and said product stream comprises dimethylbutanes and isopentanes.

14. The process of claim 1 wherein the isomerization conditions of said second reaction zone include a Liquid Hourly Space Velocity greater than the of said first reaction zone.

15. The process of claim 10 wherein the isomerization conditions of said second reaction zone include a Liquid Hourly Space Velocity greater than the Liquid Hourly Space Velocity of said first reaction zone.

16. The process of claim 1 wherein said product stream has a 2,3-dimethylbutane concentration of at least 24 wt. %.

17. The process of claim 11 wherein said product stream has a 2,3-dimethylbutane concentration of at least 24 wt. %.

* * * * *